United States Patent [19]

Fischer

[11] Plant 5,066

[45] Jul. 5, 1983

[54] AFRICAN VIOLET NAMED BIG STAR

[75] Inventor: Arnold W. Fischer, Hanover, Fed. Rep. of Germany

[73] Assignee: Pan-American Plant Company, Parrish, Fla.

[21] Appl. No.: 252,895

[22] Filed: Apr. 10, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new variety of African Violet plant distinguished by its intermittent but profusely blooming habit and its dark blue, star-shaped flowers of very large size borne as a cyme on strong, upright stems, the plant having a rapid growth rate and a compact rosette shape.

4 Drawing Figures

BACKGROUND OF THE NEW PLANT

This new African Violet variety originated as a seedling of unknown parentage growing among a group of violet plants maintained in greenhouse at Fallbrook, Calif., for breeding purposes, this plant having been discovered by me in 1977 and selected for propagation and test because of its profuse production of dark blue, star-shaped flowers of very large size. Asexual reproduction of this plant was done by means of cuttings at Fallbrook, Calif., and after further propagation through successive generations, it was determined that not only did the new plant have excellent horticultural characteristics for the commercial market but also that its novel characteristics appeared to be firmly fixed and would hold true from generation to generation. Commercial propagation of this new African Violet plant is now being done at West Chicago, Ill., and at Parrish, Fla.

DESCRIPTION OF THE DRAWINGS

This new violet plant is illustrated by the accompanying drawings, of which sheet 1 is a photographic view of a potted plant in full bloom showing the general form and arrangement of floral display, sheet 2 is a photographic print showing a full face view of a flower of this variety which has been hand-painted to show the true flower color, and sheets 3 and 4 are prints of machine copies of the front and back sides, respectively, of typical leaves of this plant.

DESCRIPTION OF THE NEW PLANT

The following is a detailed description of the new plant based upon observations made in greenhouse at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—African Violet.

Form: Compact and rosette shaped.
Growth habit: Rapid and vigorous.
Foliage:

- *Quantity.*—Abundant; about 25 leaves.
- *Size of leaf.*—Width — From insignificant to about 80 mm. Length — From insignificant to about 85 mm.
- *Shape.*—Oval with acute tip and slightly oblique base, and with repand margin.
- *Texture.*—Pubescent.
- *Aspect.*—Glossy.
- *Color.*—Upper Side — 137A. Under Side — 138D.
- *Ribs and veins.*—Pinnate.
- *Rachis.*—Length: From insignificant to about 80 mm.

THE BUD

Size: Varies in both diameter and length.
Shape: Globular.
Opening rate: Typical violet.
Color of petals:
- *When sepals first divide.*—94A.
- *When petals begin to unfurl.*—95A.

Sepals:
- *Number.*—Five.
- *Shape.*—Lanceolate and branched, becoming flat when flowers open.
- *Color.*—Inside — 199A. Outside — 199A.

Calyx:
- *Size.*—Medium.
- *Shape.*—Calyx splits to star-shaped form.
- *Aspect.*—Hairy.

Peduncle:
- *Length.*—About 105 mm.
- *Aspect.*—Hairy.
- *Character.*—Erect and rigid.
- *Color.*—199D.

THE FLOWER

Blooming habit: Intermittent with profuse production of blooms.
Size of flower: Very large.
- *Diameter.*—About 32 to 50 mm.
- *Depth.*—Flat.

Borne: As a cyme.
Shape: When bloom first opens, cup-shaped; becoming flat as bloom matures.
Petalage:
- *Number of petals.*—Five.
- *Arrangement.*—Sympetalous.

*Form.*—Actinomorphic and rotate with rounded apex and repand margin.

*Texture.*—Soft.

*Appearance.*—Satiny.

*Color.* Face Side — 95A. Reverse Side — 94C.

Peduncle:

*Length.*—From insignificant to about 105 mm.

*Character.*—Strong and upright.

*Color.*—199D.

Persistence: The flowers hang on and dry.

Fragrance: None.

Lasting quality: About 10 to 20 days on the plant for the fully opened flower.

REPRODUCTIVE ORGANS

Stamens:

*Anthers.*—Five in number with monadelphous arrangement. Size: About 3 mm. square. Color: Yellow.

*Filaments.*—Length: About 3 mm. Color: Whitish-yellow.

*Pollen.*—Color — Yellow.

Pistils:

*Number.*—One.

*Styles.*—Length: About 7 mm. Color: 95A.

*Stigma.*—Color — Whitish.

Ovaries: Hypogynous and tomentose.

This new African Violet plant is particularly distinguished by its very large, dark blue, star-shaped flowers which have excellent substance and keeping quality and its profuse production of blooms borne in a bouquet above medium green foliage.

I claim:

1. A new and distinct African Violet cultivar, substantially as herein shown and described, distinguished by its vigorous growth habit and its profuse production of very large, dark blue, star-shaped flowers atop a plant of generally rosette shape.

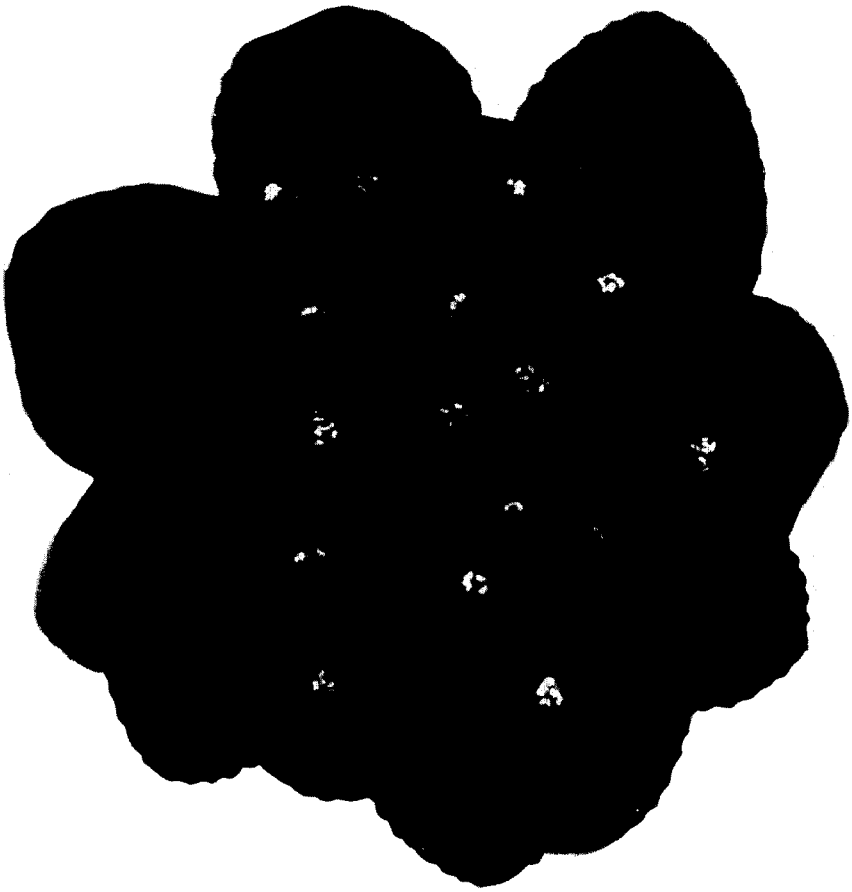

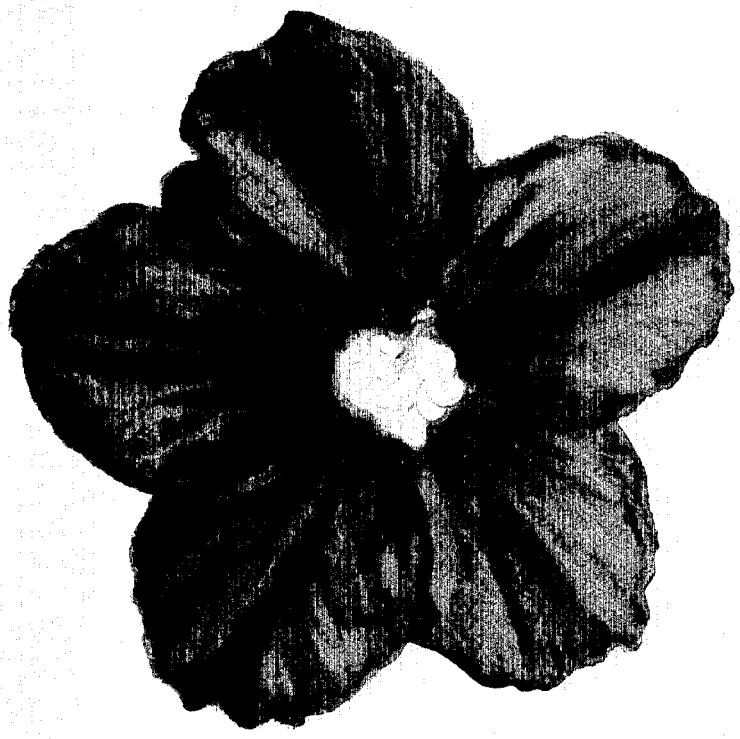

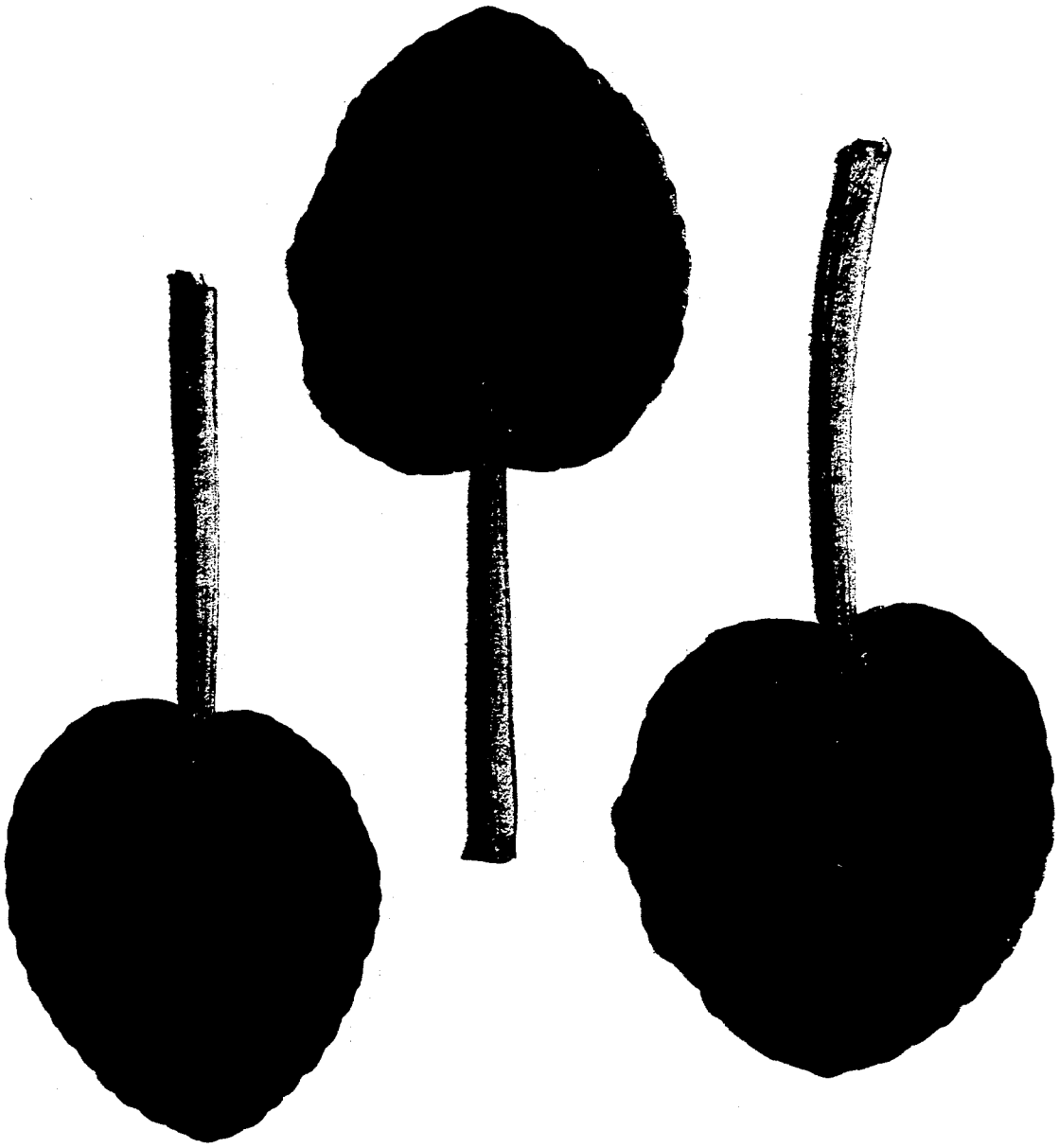

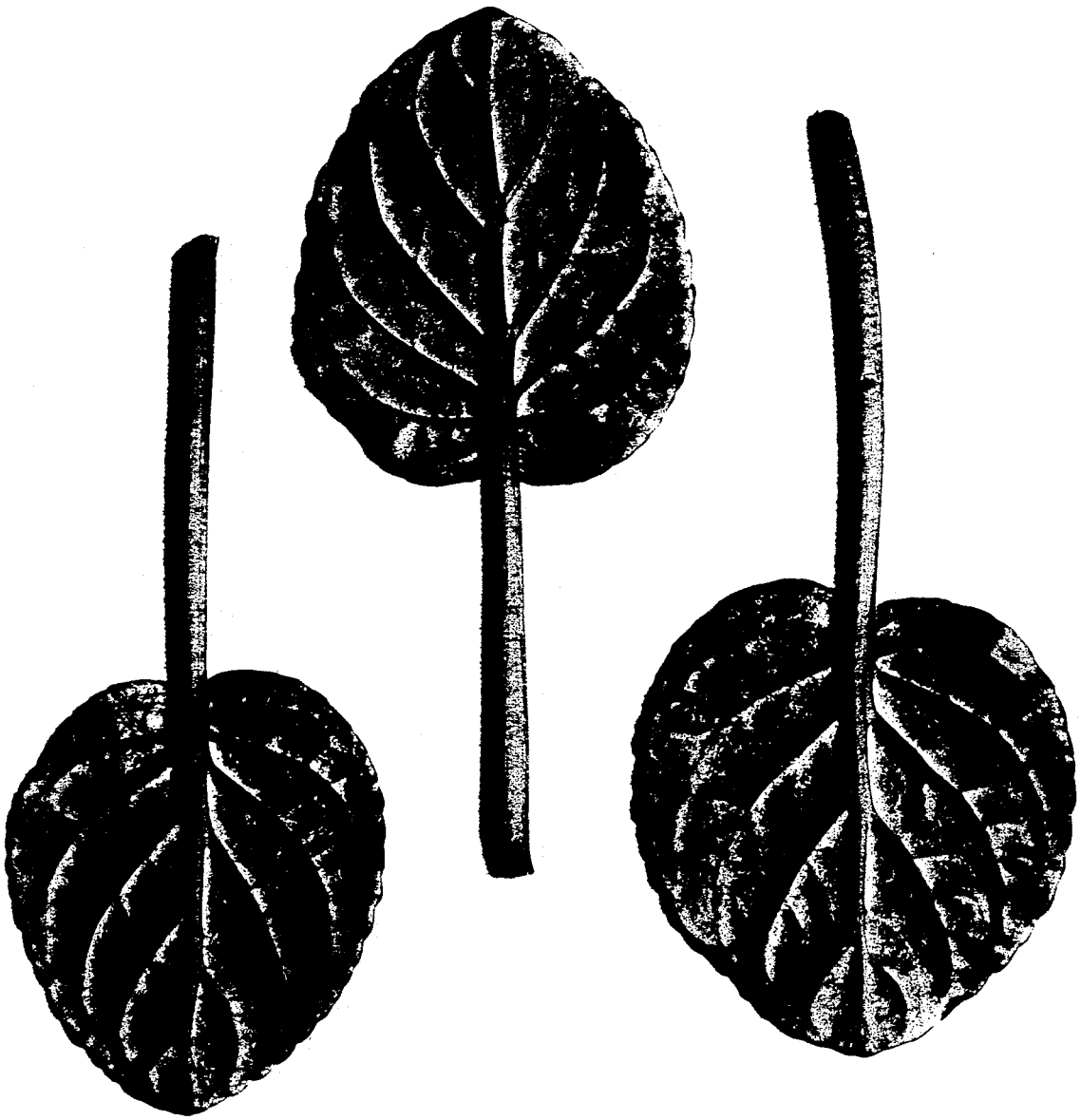

* * * * *